(12) United States Patent
Beck et al.

(10) Patent No.: US 7,238,636 B2
(45) Date of Patent: Jul. 3, 2007

(54) HIGH TEMPERATURE CALCINATION OF SELECTIVATED MOLECULAR SIEVE CATALYSTS FOR ACTIVITY AND DIFFUSIONAL MODIFICATION

(75) Inventors: Jeffrey S. Beck, Annandale, NJ (US); William G. Borghard, Haddon Heights, NJ (US); Arthur W. Chester, Cherry Hill, NJ (US); Carrie L. Kennedy, Washington, NJ (US); David L. Stern, Asbury, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 615 days.

(21) Appl. No.: 10/625,322

(22) Filed: Jul. 23, 2003

(65) Prior Publication Data

US 2005/0020435 A1    Jan. 27, 2005

(51) Int. Cl.
*B01J 20/04* (2006.01)
(52) U.S. Cl. .............................. 502/63; 502/60; 502/64; 502/66; 502/71; 502/74; 502/84; 502/85; 502/214
(58) Field of Classification Search .................. 502/60, 502/63, 64, 66, 71, 74, 84, 85, 214
See application file for complete search history.

(56) References Cited

U.S. PATENT DOCUMENTS

| | | | |
|---|---|---|---|
| 4,029,716 A | 6/1977 | Kaeding | |
| 4,049,573 A | 9/1977 | Kaeding | |
| 4,067,920 A | 1/1978 | Kaeding | |
| 4,078,009 A | 3/1978 | Kaeding | |
| 4,097,543 A | 6/1978 | Haag et al. | |
| 4,264,473 A | 4/1981 | Tu et al. | |
| 4,724,270 A | 2/1988 | Chang et al. | |
| 5,034,362 A | 7/1991 | Chu et al. | 502/60 |
| 5,243,117 A | 9/1993 | Chang et al. | |
| 5,384,296 A | 1/1995 | Tsao | 502/66 |
| 5,406,015 A | 4/1995 | Beck et al. | |
| 5,567,666 A | 10/1996 | Beck et al. | |
| 5,602,066 A | 2/1997 | Beck et al. | |
| 5,610,112 A | 3/1997 | Lago et al. | 502/63 |
| 5,689,027 A | 11/1997 | Abichandani et al. | |
| 5,726,114 A * | 3/1998 | Chang et al. | 502/64 |
| 5,849,968 A | 12/1998 | Beck et al. | 585/481 |
| 6,051,519 A | 4/2000 | Wu et al. | |
| 7,074,739 B2 * | 7/2006 | Dakka et al. | 502/214 |
| 2004/0030210 A1 * | 2/2004 | Mohr et al. | 585/446 |
| 2004/0087822 A1 * | 5/2004 | Buchanan et al. | 585/467 |
| 2004/0158111 A1 * | 8/2004 | Johnson et al. | 585/467 |

FOREIGN PATENT DOCUMENTS

EP    0 030 796    6/2001
WO    WO 98/14415    4/1998

OTHER PUBLICATIONS

Tsai, T-C et al., "Disproportionation and transalkylation of alkylbenzenes over zeolite catalyts", Applied Catalysis A: General, Elsevier Science, Amsterdam, NL, vol. 181, No. 2, pp. 355-398 (1999), no month.
Sayed, Moein et al., "The Effect of Modification with Boron on the Catalytic Activity and Selectivity of HZSM-5", *Journal of Catalysis* 101, pp. 43-55 (1986).
Young, L. B. et al., "Shape Selective Reactions with Zeolite Catalysts, III. Selectivity in Xylene Isomerization, Toluene-Methanol Alkylation, and Toluene Disproportionation over ZSM-5 Zeolite Catalysts", *Journal of Catalysis*, 76, pp. 418-432 (1982).
Kaeding, W. W. et al., "Shape-Selective Reactions with Zeolite Catalysts, II. Selective Disproportionation of Toluene to Produce Benzene and p-Xylene", Journal of Catalysis 69, pp. 392-398 (1981).
Takahashi, T. et al., "Vapor phase reaction of cyclohexanone oxime over boria modified HSZM-5 zeolites", Canadian Journal of Chemical Engineering, vol. 69, No. 5, Oct. 1991, pp. 1096-1099.
Kim, J.H. et al., "Shape Selectivity of ZSM-5 Type Zeolite for Alkylation of Ethylbenzene with Ethanol", Bulletin of the Chemical Society of Japan, vol. 61, No. 4, Apr. 1988, pp. 1051-1055.
Kim, John-Ho et al., "Para-selectivity of zeolites with MFI structure - Difference between disproportionation and alkylation", *Applied Catalysis* A vol. 83 pp. 51-58 (1992).
Sayed, Moein B. et al., "The Effect of Boron on ZSM-5 Zeolite Shape Selectivity and Activity, II. Coincorporation of Aluminum and Boron in the Zeolite Lattice", *Journal of Catalysis* vol. 116, 1-10 (1989).
Ivanova, I. I. et al., "Disproportionation of toluene on modified pentasils", Neftekhimiya, 28(4), pp. 460-7 (1988).
Meshram, Namdeo R. "Selective Toluene Disproportionation Over ZSM-5 Zeolites", J. Chem. Tech. Biotechnol., vol. 37, pp. 111-122 (1987).

* cited by examiner

Primary Examiner—Elizabeth D. Wood
(74) Attorney, Agent, or Firm—Xiaobing Feng

(57) ABSTRACT

A method is disclosed for modifying a catalytic molecular sieve for shape-selective hydrocarbon conversions comprises:
 a) selectivating said catalytic molecular sieve by contacting with a silicon-containing selectivating agent; and
 b) calcining the selectivated catalytic molecular sieve at high temperature calcination conditions comprising temperatures greater than 700° C., which conditions are sufficient to reduce acid activity as measured by alpha value and increase diffusion barrier of said catalytic molecular sieve as measured by the rate of 2,3-dimethylbutane uptake, as compared to the selectivated catalyst. Catalytic molecular sieves thus prepared, such as silica-bound ZSM-5, and their use in hydrocarbon conversion processes such as aromatics isomerization, e.g., xylene isomerization, ethylbenzene conversion and aromatics disproportionation, e.g., toluene disproportionation are also disclosed.

16 Claims, 1 Drawing Sheet

FIGURE
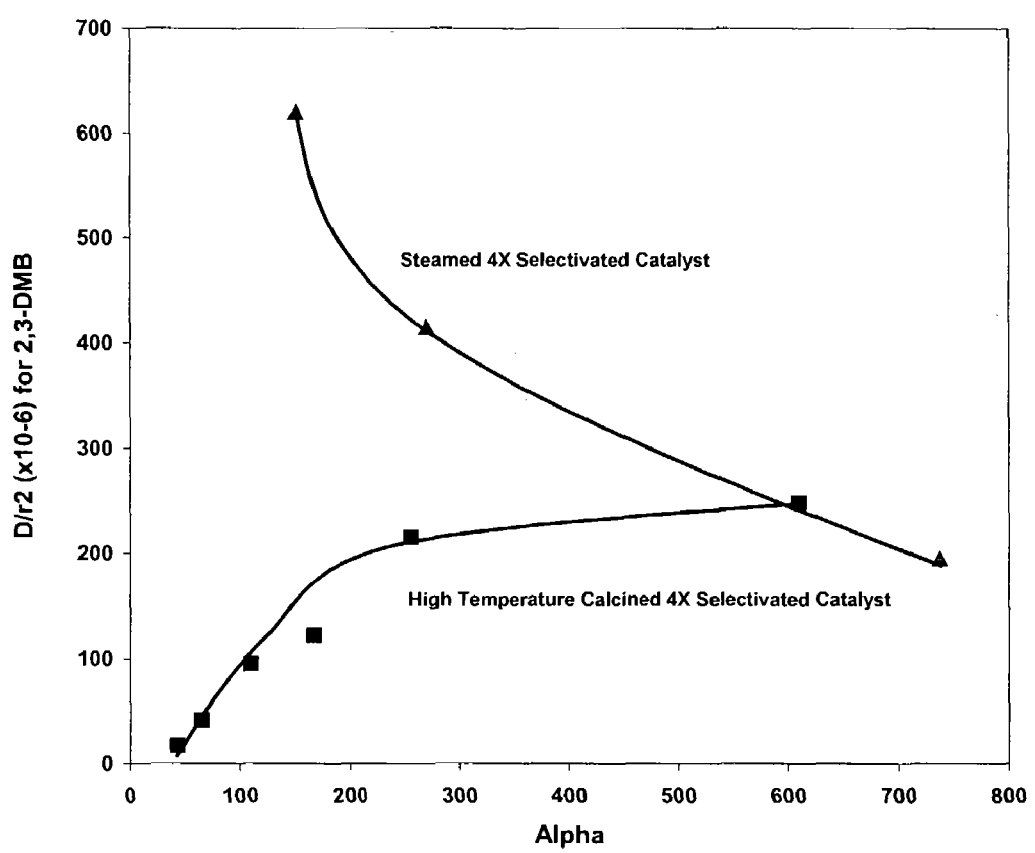

HIGH TEMPERATURE CALCINATION OF SELECTIVATED MOLECULAR SIEVE CATALYSTS FOR ACTIVITY AND DIFFUSIONAL MODIFICATION

FIELD OF THE INVENTION

The present invention relates to a process for modifying acid activity and diffusional restriction of selectivated zeolite hydrocarbon conversion catalysts, as well as the catalysts so modified, and their use in shape-selective hydrocarbon conversion.

BACKGROUND OF THE INVENTION

Diffusionally modified catalysts find use in many shape-selective, hydrocarbon processing applications. The selectivity to more desirable products (and ultimate product slate) can be modified with diffusionally restricted catalysts. Mass transport selectivity arises from a large difference in the diffusivity of the participating molecules in the zeolite channels, white transition state selectivity results from steric constraints limiting the possible transition state of the catalytic transformation step. The advantages of diffusionally modified catalysts are especially useful in certain petroleum/petrochemical industry processes including catalytic dewaxing, olefin alkylation, shape-selective cracking and aromatic conversion processes such as aromatics disproportionation, e.g., toluene disproportionation, aromatics isomerization, e.g., xylene isomenization, and para-selective aromatics alkylation. The optimum level of acidity for these reactions can vary substantially. For selective aromatics disproportionation processes, e.g., toluene disproportionation processes, a high acid level (700 alpha) can produce a high value product slate. Selective ethylbenzene conversion processes are optimized by a medium acidity level (~50 to 150 alpha), while dewaxing and para-selective aromatics alkylation processes prefer lower acid activities (~5 to 25 alpha).

Ex-situ selectivated catalysts, such as those modified via multiple silica treatments, are particularly attractive for these processes because the diffusion barrier required for optimal performance is present prior to utilization for the reaction of choice. Presently, high acid activity zeolite catalyst can be used as a base for multiple selectivation sequences, e.g., a 1000 alpha catalyst is used to produce a high acid activity toluene disproportionation catalyst, which after several selectivation treatments still has an alpha value of about 700, while diffusionally modified catalyst for other applications may require lower acid activity as noted above.

Steaming has been used to decrease acid activity of catalysts. However, steaming silica-selectivated catalysts to the lower acid activity levels required for certain applications significantly decreases the diffusional barrier, probably resulting from migration of the silica diffusion barrier during steaming.

Accordingly, it would be desirable to provide a method for modifying zeolite catalyst activity, which does not decrease the diffusion barrier of the resulting catalyst. It would further be desirable to provide a method for modifying zeolites to provide a diffusionally restricted catalyst having reduced acid activity while maintaining or increasing the diffusion barrier of the modified catalyst.

U.S. Pat. No. 5,849,968 to Beck et al. discloses a process for shape-selective hydrocarbon conversion using a zeolite catalyst selectivated with a siliceous material and treated with an aqueous solution comprising alkaline earth metal ions under ion exchange conditions. After selectivation, the zeolite is calcined at temperatures greater than 200° C., including temperatures below 700° C. U.S. Pat. No. 5,610,112 to Lago et al. discloses a process for modifying a catalytic molecular sieve by pre-selectivation to deposit a silicon compound on the external surface of the catalyst and then calcined at a temperature below 600° C. for one to 24 hours. The catalyst may then be steamed at 200° C. to 538° C. to provide improved selectivity. U.S. Pat. No. 5,726,114 to Chang et al. discloses a method for modifying catalytic molecular sieve to enhance shape selectivity by exposing to at least one ex situ selectivation sequence which includes impregnation of the molecular sieve with a selectivating agent in an aqueous emulsion and a subsequent calcination of the impregnated molecular sieve at temperatures below 600° C. U.S. Pat. No. 5,384,296 to Tsao discloses a thermally stable noble metal-containing zeolite catalyst which has increased resistance to noble metal agglomeration as a result of calcining at at least 600° C. in moist air. U.S. Pat. No. 5,034,362 to Chu et al. discloses a zeolite catalyst composition having improved shaped selectivity which has been calcined at a temperature of at least 649° C. which is useful for aromatic conversion reactions. None of these disclosures teach or suggest the use of very high temperature calcination as a means to modify acid activity of selectivated molecular sieves without decreasing diffusional resistance of the modified catalyst.

SUMMARY OF THE INVENTION

The present invention relates to a method for modifying a catalytic molecular sieve, e.g., for shape-selective hydrocarbon conversions, which comprises:

a) selectivating said catalytic molecular sieve by contacting with a silicon-containing selectivating agent; and b) calcining the selectivated catalytic molecular sieve at high temperature calcination conditions comprising temperatures greater than 700° C., which conditions are sufficient to reduce acid activity as measured by alpha value and increase diffusion barrier of said catalytic molecular sieve as measured by the rate of 2,3-dimethylbutane uptake, as compared to the selectivated catalyst, e.g., increasing said diffusion barrier by at least 25%, at least 35%, at least 50% or more.

In another aspect, the present invention relates to a method for shape-selective hydrocarbon conversion which comprises:

i) selectivating a catalytic molecular sieve by contacting with a silicon-containing selectivating agent;

ii) calcining the selectivated catalytic molecular sieve at high temperature calcination conditions comprising temperatures greater than 700° C., which conditions are sufficient to reduce acid activity as measured by alpha value and increase diffusion barrier of said catalytic molecular sieve as measured by the rate of 2,3-dimethylbutane uptake, as compared to the selectivated catalytic molecular sieve, to provide a high temperature calcined catalytic molecular sieve, and iii) contacting a hydrocarbon feed under hydrocarbon conversion conditions with said high temperature calcined catalytic molecular sieve.

DETAILED DESCRIPTION OF THE INVENTION

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Catalysts

The catalytic molecular sieve used in the present invention can be a zeolite, e.g., an intermediate pore-size zeolite having a constraint index within the approximate range of 1 to 12 (e.g., zeolites having less than about 7 angstroms pore size, such as from about 5 to less than 7 angstroms) having a silica to alumina mole ratio of at least about 5, e.g., at least about 12, e.g., at least 20.

The silica to alumina mole ratio referred to may be determined by conventional analysis. This ratio is meant to represent, as closely as possible, the molar ratio in the rigid anionic framework of the zeolite crystal and to exclude silicon and aluminum in the binder or in cationic or other form within the channels.

Examples of intermediate pore size zeolites useful in this invention include ZSM-5 (U.S. Pat. No. 3,702,886) and U.S. Pat. No. Re. 29,948); ZSM-11 (U.S. Pat. No. 3,709,979), ZSM-5/ZSM-11 intermediate (U.S. Pat. No. 3,832,449); ZSM-12 (U.S. Pat. No. 3,832,449); ZSM-22 (U.S. Pat. No. 4,556,477); ZSM-23 (U.S. Pat. No. 4,076,842); ZSM-35 (U.S. Pat. No. 4,016,245); ZSM-48 (U.S. Pat. No. 4,397,827); ZSM-50 (U.S. Pat. No. 4,640,829; ZSM-57 (U.S. Pat. No. 5,046,685); and/or ZSM-58 (U.S. Pat. No. 5,417,780).

Other zeolites suitable for use in some embodiments of the present invention include zeolite beta, MCM-22 (U.S. Pat. No. 5,304,968), MCM-36 (U.S. Pat. No. 5,292,698), MCM-49 (U.S. Pat. No. 5,236,575), MCM-56 (U.S. Pat. No. 5,362,697), mordenite, MCM-58 (U.S. Pat. No. 5,437,855), synthetic and natural faujasites, and amorphous or ordered mesoporous materials such as MCM-41 (U.S. Pat. No. 5,098,684).

Additional molecular sieves which find utility in conjunction with the present invention include aluminophosphates, e.g., ALPO-5, VPI-5; silicoaluminophosphates, e.g., SAPO-5, SAPO-11, SAPO-30, SAPO-31, SAPO-34; and other metal aluminophosphates. These are variously described in U.S. Pat. Nos. 4,440,871; 4,554,143; 4,567,029; 4,666,875; and 4,742,033.

Further additional molecular sieves which find utility in the present invention include ITQ-2, ITQ-3 (described in U.S. Pat. No. 6,500,404), ITQ-12 (described in U.S. Pat. No. 6,471,939), and ITQ-13 (described in U.S. Pat. No. 6,471,941). The structural types and references to the synthesis of these zeolites can be found in the "Atlas of Zeolite Framework Types" (published on behalf of the Structure Commission of the International Zeolite Association), by Ch. Caerlocher, W. M. Meier, and D. H. Olson, published by Elsevier, Fifth revised edition, 2002, which is hereby incorporated by reference. Structural types and references to the zeolites mentioned above are available on the World Wide Web at www.iza-structure.org. Such zeolites are commercially available from Zeolyst International, Inc.

Alpha Value Measurement

The alpha value of a catalyst is an approximate indication of the catalytic cracking activity of the catalyst compared to a standard catalyst, and it gives the relative rate constant (rate of normal hexane conversion per volume of catalyst per unit time). It is based on the activity of the amorphous silica-alumina cracking catalyst taken as an alpha of 1 (Rate Constant=0.016 sec$^{-1}$). The alpha test is described in U.S. Pat. No. 3,354,078 and in the Journal of Catalysis, 4, 522–529 (1965); 6, 278 (1966); and 61, 395 (1980), each incorporated herein by reference as to that description. It is noted that intrinsic rate constants for many acid-catalyzed reactions are proportional to the alpha value for a particular crystalline silicate catalyst (see The Active Site of Acidic Aluminosilicate Catalysts. Nature, Vol. 309, No. 5959, 589–591, (1984)). The experimental conditions of the test used herein include a constant temperature of 538° C. and a variable flow rate as described in detail in the Journal of Catalysis, 61, 395 (1980). The catalysts employed in the process of the present invention can have an alpha value less than 700, preferably 25 to 200, say, 75 to 150, 5 to 25 (for lower acid activity processes such as aromatics alkylation), and a silica-alumina ratio less than 100, preferably 20–80. The alpha value of the catalyst may be increased by initially treating the catalyst with nitric acid or by mild steaming before selectivation as discussed in U.S. Pat No. 4,326,994. Generally, the present invention relates to reducing the alpha value of catalyst as prepared to tailor it to the specific application in which it is to be used, without significantly reducing the diffusional barrier of the catalyst (say, by more than 5 or 10%). Indeed, in most instances, alpha value is reduced while actually increasing the diffusional barrier. This represents a significant improvement in controlling catalyst selectivity and activity inasmuch as steaming to reduce alpha value significantly reduces the diffusional barrier.

Diffusion Barrier Measurement

As used herein, the Diffusion Parameter of a particular porous crystalline material is defined as $D/(r^2 \times 10^6)$, wherein D is the diffusion coefficient (cm$^2$/sec) and r is the crystal radius (cm). The required diffusion parameters can be derived from sorption measurements provided the assumption is made that the plane sheet model describes the diffusion process. Thus for a given sorbate loading Q, the value $Q/Q_\infty$, where $Q_\infty$ is the equilibrium sorbate loading, is mathematically related to $(Dt/r^2)^{1/2}$ where t is the time (sec) required to reach the sorbate loading Q. Graphical solutions for the plane sheet model are given by J. Crank in "The Mathematics of Diffusion", Oxford University Press, Ely House, London, 1957.

The apparatus and procedures for performing static and dynamic adsorption measurements are described in G. R. Landolt, Anal. Chem. (1971) 43, 613, and E. L. Wu, G. R. Landolt, and A. W. Chester, "Hydrocarbon Adsorption Characterization of Some High Silica-Zeolites," Stud. Surf. Science & Catal. 28, p. 547. Changes in the diffusion barrier resulting from high temperature calcination can be monitored by observing the Diffusion Parameter as described above. The values thereof are based on the rate of uptake of sorbate 2,3-dimethylbutane (or bulkier 2,2-dimethylbutane for lower diffusion barriers). Equilibrium capacity of the diffusing medium is determined according to Crank's solution to diffusion in a porous body having flat plate geometry. With proper adjustment, the equilibrium capacity may be estimated from values of a more rapidly diffusing molecule, e.g., n-hexane. The n-hexane isotherms are measured at 90° C. and the amount sorbed at 75 torr taken as sorption capacity. Nominal experimental conditions for obtaining diffusivity measurements with 2,3-dimethylbutane are 120° C. and 44 torr. The weight uptake of 2,3-dimethylbutane versus the square root of time is plotted from which the rate is obtained and $D/(r^2 \times 10^6)$ is calculated.

Catalyst Binder

The catalysts of the present invention can optionally be employed in combination with a support or binder material (binder). The binder is preferably an inert, non-alumina containing material, such as a porous inorganic oxide support or a clay binder. One such preferred inorganic oxide is silica. Other examples of such binder material include, but are not limited to zirconia, magnesia, titania, thoria and boria. These materials can be utilized in the form of a dried inorganic oxide gel or as a gelatinous precipitate. Suitable examples of clay binder materials include, but are not limited to, bentonite and kieselguhr. The relative proportion of catalyst to binder material to be utilized is from about 30 wt. % to about 98 wt. %. A proportion of catalyst to binder from about 50 wt. % to about 80 wt. % is more preferred. The bound catalyst can be in the form of an extrudate, beads or fluidizable microspheres.

Cation Exchanged Zeolites

The catalyst may be associated with hydrogen, e.g., hydrogen-exchanged zeolite, or the catalyst may be associated with a hydrogenation component (hydrogenation-dehydrogenation component, e.g., hydrogenation metal). Examples of such components include the oxide, hydroxide, sulfide, or free metal (i.e., zero valent) forms of Group VIIA metals (i.e., Pt, Pd, Ir, Rh, Os, Ru, Ni, Co and Fe), Group VIIA metals (i.e., Mn, Tc, and Re), Group VIA metals (i.e., Cr, Mo, and W), Group VB metals (i.e., Sb and Bi), Group IVB metals (i.e., Sn and Pb), Group IIB metals (i.e., Ga and In), Group IIA metal, (e.g., Zn) and Group IB metals (i.e., Cu, Ag and Au). Noble metals (i.e., Pt, Pd, Ir, Rh, Os and Ru) are preferred hydrogenation components. Combinations of catalytic forms of such noble or non-noble metal, such as combinations of Pt with Sn, may be used. The metal may be in a reduced valence state, e.g., when this component is in the form of an oxide or hydroxide. The reduced valence state of this metal may be attained, in situ, during the course of a reaction, when a reducing agent, such as hydrogen, is included in the feed to the reaction.

The hydrogenation component may be incorporated into the catalyst by methods known in the art, such as ion exchange, impregnation or physical admixture. For example, solutions of appropriate metal salts may be contacted with the remaining catalyst components, either before or after selectivation of the catalyst, under conditions sufficient to combine the respective components. The metal-containing salt may be water soluble. Examples of such salts include chloroplatinic acid, tetraamineplatinum complexes, platinum chloride, tin sulfate and tin chloride. The metal may be incorporated in the form of a cationic, anionic or neutral complex and cationic complexes such as Pt $(NH_3)_4^{2+}$ of this type will be found convenient for exchanging metals onto the zeolite. For example, a platinum modified catalyst can be prepared by first adding the catalyst to a solution of ammonium nitrate in order to convert the catalyst to the ammonium form. The catalyst is subsequently contacted with an aqueous solution of tetraamine platinum(II) nitrate or tetraaamine platinum(II) chloride. Anionic complexes such as the vanadate or metatungstate ions are also useful for impregnating metals into the zeolites. Incorporation may be undertaken in accordance with the invention of U.S. Pat. No. 4,312,790, incorporated by reference herein. After incorporation of the metal, the catalyst can then be filtered, washed with water and calcined at temperatures of from about 250° C. to about 500° C.

The amount of hydrogenation component may be that amount which imparts or increases the catalytic ability of the overall catalyst to catalytically hydrogenate or dehydrogenate an organic compound under sufficient hydrogenation or dehydrogenation conditions, e.g., hydrogenate ethylene to ethane. This amount is referred to as a catalytic amount. The amount of the hydrogenation component may be from 0.001 to 10 percent by weight, although this will, of course, vary with the nature of the component, with less of the highly active noble metals, particularly platinum, being required than of the less active base metals.

Catalyst Selectivation

The catalyst of the present invention can be selectivated by a vapor phase process or a liquid phase process. An example of a liquid phase selectivation process is described herein as an ex situ selectivation process. Examples of ex situ selectivation techniques suitable for use in the present invention are provided in U.S. Pat. Nos. 5,367,099; 5,404,800; and 5,365,004. The ex situ selectivation treatment may result in the deposition of at least 1 wt. % of siliceous material on the zeolite. The treatment deposits siliceous material on the catalyst by contacting the catalyst with a silicon-containing selectivating agent. Subsequent to treatment with the selectivating agent, the catalyst may be conventionally calcined at temperatures, below, say, 600° C. or less, under conditions sufficient to remove organic material therefrom while leaving the siliceous material on the zeolite, preferably without reducing the crystallinity of the zeolite.

The catalyst may be ex situ selectivated by single or multiple treatments with a liquid organosilicon compound in a liquid carrier. Each treatment can be followed by calcination of the treated material in an oxygen-containing atmosphere, e.g., air.

In accordance with the multiple impregnation ex situ selectivation method, the zeolite is treated at least twice, e.g., from 2 to 6 times, with a liquid medium comprising a liquid carrier and at least one liquid organosilicon compound. The organosilicon compound may be present in the form of a solute dissolved in the liquid carrier or in the form of emulsified droplets in the liquid carrier. For the purposes of the present disclosure, it will be understood that a normally solid organosilicon compound will be considered to be a liquid (i.e., in the liquid state) when it is dissolved or emulsified in a liquid medium. The liquid carrier may be water, an organic liquid or a combination of water and an organic liquid. Particularly when the liquid medium comprises an emulsion of the organosilicon compound in water, the liquid medium may also comprise an emulsifying agent, such as a surfactant. Stable aqueous emulsions of organosilicon compounds (e.g., silicone oil) suitable for use in the present invention are described in U.S. Pat. No. 5,726,114 to Chang et al. These emulsions are generated by mixing the organosilicon oil and an aqueous component in the presence of a surfactant or surfactant mixture. Useful surfactants include any of a large variety of surfactants, including ionic and non-ionic surfactants. Preferred surfactants include non-nitrogenous, non-ionic surfactants such as alcohol, alkylphenol, and polyalkoxyalkanol derivatives, glycerol esters, polyoxyethylene esters, anhydrosorbitol esters, ethoxylated anhydrosorbitol esters, natural fats, oils, waxes and ethoxylated esters thereof, glycol esters, polyalkylene oxide block co-polymer surfactants, poly(oxyethylene-co-oxypropylene) non-ionic surfactants, and mixtures thereof. More preferred surfactants include octoxynols such as Octoxynol-9. Such preferred surfactants include the TRITON® X series, such as TRITON® X-100 and TRITON® X-305, available from Rohm & Haas Co., Philadelphia, Pa., and the Igepal® Calif series from GAF Corp., New York, N.Y. Emulsions formulated using such surfactants are effective for selectivating zeolites such as ZSM-5 to enhance shape selectivity, and to passivate surface acidity detrimental to product selectivity in certain regioselective catalytic applications such as the disproportionation of alkylbenzenes. Organosilicon compounds useful herein are water soluble and may be described as organopolysiloxanes. The preferred compounds are polyalkylene oxide modified organopolysiloxanes. The organopolysiloxanes are preferably larger than the pores of the catalyst and do not enter the pores.

The organosiliocon compound selectivating agent may be, for example, a silicone, a siloxane, a silane or mixtures thereof. These organosilicon compounds may have at least 2 silicon atoms per molecule. These organosilicon compounds may be solids in pure form, provided that they are soluble or otherwise convertible to the liquid form upon combination with the liquid carrier medium. The molecular weight of the silicone, siloxane or silane compound employed as a preselectivating agent may be between about 80 and about 20,000, and preferably within the approximate range of 150 to 10,000. Suitable silicon-containing selectivating agent is selected from the group consisting of polysiloxanes, siloxanes, silanes, disilanes and alkoxysilanes. Representative ex situ selectivation silicone compounds include dimethyl silicone, diethyl silicone, phenylmethyl silicone, methylhydrogen silicone, ethylhydrogen silicone, phenylhydrogen silicone, methylethyl silicone, phenylethylsilicone, diphenyl silicone, methyltrifluoropropyl silicone, ethyltrifluoropropyl silicone, polydimethyl silicone, tetrachlorophenylmethyl silicone, tetrachlorophenylethyl silicone, tetrachlorophenylhydrogen silicone, tetrachlorophenyl silicone, methylvinyl silicone, and ethylvinyl silicone. The ex situ selectivating silicone, siloxane or silane compound need not be linear, but may be cyclic, for example, hexamethyl cyclotrisiloxane, octamethyl cyclotetrasiloxane, hexaphenyl cyclotrisiloxane and octaphenyl cyclotetrasiloxane. Mixtures of these compounds may also be used as liquid ex situ selectivating agents, as may silicones with other functional groups.

Preferred silicon-containing selectivating agents, particularly when the ex situ selectivating agent is dissolved in an organic carrier or emulsified in an aqueous carrier, include dimethylphenylmethylpolysiloxane (e.g., Dow-550®) and phenylmethyl polysiloxane (e.g., Dow-710®). Dow-550® and Dow-710® are available from Dow Chemical Company, Midland, Mich.

Water soluble organosilicon compounds are commercially available as, for example, SAG-5300®, manufactured by Union Carbide, Danbury Conn., conventionally used as an anti-foam, and SF 1188® manufactured by General Electric, Pittsfield, Mass.

When the organosilicon ex situ selectivating agent is present in the form of a water soluble compound in an aqueous solution, the organosilicon may be substituted with one or more hydrophilic functional groups or moieties, which serve to promote the overall water solubility of the organosilicon compound. These hydrophilic functional groups may include one or more organoamine groups, such as —$N(CH_3)_3$, —$N(C_2H_5)_3$, and —$N(C_3H_7)_3$. A preferred water soluble organosilicon preselectivating agent is an n-propylamine silane, available as Hydrosil 2627® from Creanova (formerly Huls America), Somerset, N.J.

The organosilicon compound can be preferably dissolved in an aqueous solution in an organosilicon compound/$H_2O$ weight ratio of from about 1/100 to about 1/1.

A "solution" is intended to mean a uniformly dispersed mixture of one or more substances at the molecular or ionic level. The skilled artisan will recognize that solutions, both ideal and colloidal, differ from emulsions.

The catalyst can be contacted with a substantially aqueous solution of the organosilicon compound at a catalyst/organosilicon compound weight ratio of from about 100 to about 1, at a temperature of about 10° C. to about 150° C., at a pressure of about 0 psig to about 200 psig, for a time of about 0.1 hour to about 24 hours, the water is preferably removed, e.g., by distillation, or evaporation with or without vacuum, and the catalyst is calcined.

Additional suitable ex situ selectivating agents for the present invention are disclosed in U.S. Pat. No. 5,849,968 to Beck et al.

Selectivation is carried out on the catalyst, e.g., by conventional ex situ treatments of the catalyst before loading into a hydrocarbon conversion reactor. Multiple ex situ treatments, say, 2 to 6 treatments, preferably 2 to 4 treatments, have been found especially useful to selectivate the catalyst. When the zeolite is ex situ selectivated by a single or multiple impregnation technique, the zeolite is calcined after each impregnation to remove the carrier and to convert the liquid organosilicon compound to a solid residue material thereof. This solid residue material is referred to herein as a siliceous solid material, insofar as this material is believed to be a polymeric species having a high content of silicon atoms in the various structures thereof, resulting from the residue of the organo portion of the organosilicon compound used to impregnate the catalyst.

Following each impregnation, the zeolite may be calcined at a rate of from about 0.2° C./minute to about 5° C./minute to a temperature greater than 200° C., but below the temperature at which the crystallinity of the zeolite is adversely affected. This conventional calcination temperature is below 700° C., e.g., within the approximate range of 350° C. to 550° C. The duration of calcination at the calcination temperature may be from 1 to 24 hours, e.g., from 2 to 6 hours.

The impregnated zeolite may be calcined in an inert or oxidizing atmosphere. An example of such an inert atmosphere is a nitrogen, i.e., $N_2$, atmosphere. An example of an oxidizing atmosphere is an oxygen containing atmosphere, such as air. Calcination may take place initially in an inert, e.g., $N_2$, atmosphere, followed by calcination in an oxygen containing atmosphere, such as air or a mixture of air and $N_2$. Calcination should be performed in an atmosphere substantially free of water vapor to avoid undesirable uncontrolled steaming of the zeolite. The zeolite may be calcined once or more than once following each impregnation. The various conventional calcinations following each impregnation need not be identical, but may vary with respect to the temperature, the rate of temperature rise, the atmosphere and the duration of calcination.

The amount of siliceous residue material which is deposited on the zeolite or bound zeolite is dependent upon a number of factors including the temperatures of the impregnation and calcination steps, the concentration of the organosilicon compound in the carrying medium, the degree to which the catalyst has been dried prior to contact with the organosilicon compound, the atmosphere used in the calcination and duration of the calcination.

High Temperature Calcination

Subsequent to the selectivating procedure(s) and any conventional calcination associated therewith, the selectivated catalyst of the present invention is subjected to a severe, high temperature, calcination treatment. Crystallinity can be measured by hexane uptake (percent crystallinity for hexane uptake calculated as hexane uptake of sample divided by hexane uptake of uncalcined sample). Crystallinity can also be measured by X-ray diffraction.

The high temperature calcining step can be carried out under conditions sufficient to provide a catalyst having an alpha value of less than 700, preferably less than 250, say, from 75 to 150, or 5 to 25, depending on the catalyst application, a crystallinity as measured by X-ray diffraction of no less than 85%, preferably no less than 95%, and a diffusion barrier of the catalytic molecular sieve as measured by the rate of 2,3-dimethylbutane or 2,2-dimethylbutane uptake of less than 270, preferably less than 150 ($D/(r^2 \times 10^6$ sec)).

The high temperature calcining step can be carried out at temperatures ranging from greater than 700° C. to 1200° C. for 0.1 to 12 hours, e.g., from 750° C. to 1000° C. for 0.3 to 2 hours, preferably from 750° C. to 1000° C. for 0.5 to 1 hours.

The selectivated zeolite may be high temperature calcined in an inert atmosphere, an oxidizing atmosphere, or a mixture of both. An example of such an inert atmosphere is nitrogen, i.e., $N_2$. An example of an oxidizing atmosphere is an oxygen containing atmosphere, such as air. Alternatively, calcination may take place initially in an inert, e.g., $N_2$, atmosphere, followed by calcination in an oxygen containing atmosphere, such as air or a mixture of air and $N_2$, or vice versa. Calcination should be performed in an atmosphere substantially free of water vapor to avoid undesirable uncontrolled steaming of the zeolite. Thus, the high temperature calcining step is preferably carried out in the absence of intentionally added steam.

Shape Selective Conversions

Zeolites modified in accordance with the invention are generally useful as catalysts in shape selective hydrocarbon conversion processes including cracking reactions, including those involving dewaxing of hydrocarbon feedstocks; isomerization of alkylaromatics, e.g., xylene isomerization; oligomerization of olefins to form gasoline, distillate, lube oils or chemicals; alkylation of aromatics; transalkylation of aromatics, e.g. toluene disproportionation; conversion or oxygenates to hydrocarbons; rearrangement of oxygenates; and conversion of light paraffins and olefins to aromatics, e.g., naphtha reforming. Non-limiting examples include: cracking hydrocarbons with reaction conditions including a temperature of from about 300° C. to about 700° C., a pressure of from about 0.1 atmosphere to about 30 atmospheres and weight hourly space velocity of from about 0.1 $hr^{-1}$ to about 20 $hr^{-1}$; dehydrogenating hydrocarbon compounds with reaction conditions including a temperature of from about 300° C. to about 700° C., a pressure of from about 0.1 atmosphere to about 10 atmospheres and weight hourly space velocity of from about 0.1 $hr^{-1}$ to about 20 $hr^{-1}$; converting paraffins to aromatics with reaction conditions including from about 300° C. to about 700° C., a pressure of from about 0.1 atmosphere to about 60 atmospheres and weight hourly space velocity of from about 0.5 $hr^{-1}$ to about 400 $hr^{-1}$ and a hydrogen/hydrocarbon mole ratio of from about 0 to about 20; convening olefins to aromatics, e.g., benzene, toluene and xylene, with reaction conditions including a temperature from about 100° C. to about 700° C., a pressure of from about 0.1 atmosphere to about 60 atmospheres, weight hourly space velocity of from about 0.5 $hr^{-1}$ to about 400 $hr^{-1}$, and a hydrogen/hydrocarbon mole ratio of from about 0 to about 20; convening alcohols, e.g., methanol, or others, e.g., dimethylether, or mixtures thereof to hydrocarbons, including olefins and/or aromatics with reaction conditions including a temperature from about 275° C. to about 600° C., a pressure of from about 0.5 atmosphere to about 50 atmospheres, weight hourly space velocity of from about 0.5 $hr^{-1}$ to about 100 $hr^{-1}$; isomerizing xylene feedstock components with reaction conditions including a temperature from about 230° C. to about 510° C., a pressure of from about 3 atmosphere to about 35 atmospheres, weight hourly space velocity of from about 0.1 $hr^{-1}$ to about 200 $hr^{-1}$, and a hydrogen/hydrocarbon mole ratio of from about 0 to about 100; disproportionating toluene with reaction conditions including a temperature from about 200° C. to about 760° C., a pressure of from about atmospheric to about 60 atmospheres, weight hourly space velocity of from about 0.08 $hr^{-1}$ to about 20 $hr^{-1}$; alkylating aromatic hydrocarbons, e.g., benzene and alkylbenzenes in the presence of an alkylating agent, e.g., olefins, formaldehyde, alkyl halides and alcohols, with reaction conditions including a temperature from about 250° C. to about 500° C., a pressure of from about atmospheric to about 200 atmospheres, weight hourly space velocity of from about 2 $hr^{-1}$ to about 2000 $hr^{-1}$, and an aromatic hydrocarbon/alkylating agent mole ratio of from about 1/1 to about 20/1; and transalkylating aromatic hydrocarbons in the presence of polyalkylaromatic hydrocarbons with reaction conditions including a temperature from about 340° C. to about 500° C., a pressure of from about atmospheric to about 200 atmospheres, weight hourly space velocity of from about 10 $hr^{-1}$ to about 1000 $hr^{-1}$, and an aromatic hydrocarbon/polyalkylaromatic hydrocarbon mole ratio of from about 1/1 to about 16/1. Additional conditions for using selectivated catalysts are set out in U.S. Pat. No. 5,455,213 to Chang et al.

In general, therefore, catalytic conversion conditions over a catalyst comprising the modified zeolite prepared by the present method include a temperature from about 100° C. to about 760° C., a pressure of from about 0.1 atmosphere to about 200 atmospheres, weight hourly space velocity of from about 0.08 $hr^{-1}$ to about 2000 $hr^{-1}$, and a hydrogen/organic, e.g., hydrocarbon compound, molar ratio of from about 0 to about 100.

All of the foregoing U.S. patents are incorporated herein by reference.

The following examples will serve to further illustrate processes and some advantages of the present invention.

EXAMPLE 1

Silicone Selectivation Treatment of ZSM-5 Catalysts

High activity ZSM-5, 65 wt. %/35 wt. % silica bound were selectivated by four consecutive silicone selectivation treatments. To this catalyst, 0.1 wt. % Pt was added via incipient wetness impregnation with $Pt(NH_3)_4(NO_3)_2$, followed by calcination.

The selectivated catalysts exhibited the following characteristics: alpha=610; 2,3-DMB ($\times 10^{-6}$ $sec^{-1}$)=248, and crystallinity based on n-hexane sorption of 99.8%.

EXAMPLE 2

High Temperature Calcination of Silicone-Selectivated ZSM-5

High temperature calcinations of a selectivated product of Example 1 were performed in a horizontal tube furnace. A quartz tube was placed in the furnace, whose length extended a few inches beyond the furnace itself, to both hold the catalyst sample boat and to allow for controlling the atmosphere in the catalyst bed during treatment. Air, pre-dried over $CaCl_2$ and activated sieves, was flowed through the tube during calcination at about 0.5 liter air/minute. The catalyst was placed in a quartz boat, which contained an internal thermowell for monitoring the actual catalyst bed temperature, then placed within the quartz tube to initiate the high temperature treatment. Treatment time is defined as follows: start time is when catalyst temperature is within 5.6° C. (10° F.) of stated temperature. Following calcination treatment, the quartz boat was removed from the furnace and allowed to cool to room temperature quickly. The results are set out in Table 1 below.

All dynamic measurements were obtained with a High Resolution Thermogravimetric Analyzer (TA Instruments Model 2950) equipped with an evolved gas furnace, a gas switching accessory and an automatic sample changer. A hydrocarbon sparging system consisting of mass flow controllers heating mantle, condenser, and circulating bath delivered the sorbates. During the sorption experiment a helium purge gas entered the balance head and blended with a sorbate carried by helium which entered through the furnace inlet tube. The carrier gas sparged through the sorbate which was maintained at a specified temperature. The flow rate of the two gas streams were controlled by mass flow controllers and were adjusted to achieve the desired partial pressures.

All static measurements were performed on a sorption system from VTI Corp. (Model MB 300). This PC controlled system consisted of an integrated microbalance from Cahn (Model D200), furnace, constant temperature bath, vacuum system and gas manifold. Adsorption isotherms were obtained by selecting a starting point of the isotherm pressure step, maximum pressure, equilibrium criteria and experimental temperature. The program provided for automatic outgassing of the sample followed by sorption of organic vapor, i.e., n-hexane.

TABLE 1

| Calc. Temp (° F.) | Time (Hours) | Alpha | 2,3-D/$r^2$ ($\times 10^{-6}$ sec$^{-1}$) | % Crystallinity (hexane sorption) |
|---|---|---|---|---|
| None | None | 610 | 248 | 100 |
| 1400 | 1 | 256 | 215 | 100 |
| 1500 | 1 | 167 | 122 | 99 |
| 1600 | 1 | 110 | 95 | 98 |
| 1700 | 1 | 65 | 41 | 96 |
| 1800 | 0.5 | 43 | 17 | 95 |

The results presented in Table 1 show that high temperature treatment of diffusionally modified catalysts can decrease acid activity, as measure by alpha, as well as substantially increase diffusional resistance (lower D/$r^2$ represents an increase in diffusional resistance). Thus, calcination at 1600° F. (871° C.) for one hour decreases alpha (from 610 to 110), but increases the diffusional resistance over two-fold. This contrasts with the results presented in Table 2 below for steam treatment, in which a similar decrease in alpha results in a net decrease in diffusional resistance. Note that the diffusional resistance of the 1800° F. (982° C.) calcined sample has increased fifteen-fold, a very significant increase in diffusional resistance over the untreated catalyst.

EXAMPLE 3

Preparation of Steamed, Uncalcined ZSM-5 (Comparative)

Steam treatments of a selectivated product of Example 1 were preformed in the same furnace setup as in the previous Example. The atmosphere through the quartz tube was steam, generated by boiling water. Steaming temperature. steam time, and alpha values and 2,3-dimethylbutane diffusivity measurements taken according to the above-described procedures are set out below in Table 2. The results show that steam treatment can be used to decrease acid activity, as measured by alpha. However, the steam treatment also decreases the diffusional resistance (higher D/$r^2$ values represent a decreased diffusional resistance).

TABLE 2

| Steaming T (° F.) | Steam Time (hours) | Alpha | 2,3-DMB D/$r^2$ ($\times 10^{-6}$ sec$^{-1}$) |
|---|---|---|---|
| None | None | 737 | 195 |
| 800 | 20 | 270 | 415 |
| 800 | 26 | 151 | 620 |

EXAMPLE 4

Comparison of High Temperature Calcination Treatment Versus Steam Treatment for Modifying 4× Selectivated Catalysts The data from Examples 2 and 3 are plotted in the Figure. They clearly show that high temperature calcination results in an increase in diffusional resistance (lower D/$r^2$) with lower acidity (as measured by alpha). In contrast, when steaming, which is a standard method for decreasing acidity (as measured by alpha), is applied to the catalyst, the diffusional resistance decreases (higher D/$r^2$). This clearly shows both the difference in these two treatments for modifying acidity, as well as the utility of this invention—that more diffusionally resistant catalysts can be produced using the high temperature calcination method.

EXAMPLE 5

Hydrocarbon Conversion Process Using High Temperature Calcined, Selectivated ZSM-5 and Steamed ZSM-5

Two catalysts were prepared for this example in accordance with the previous Examples. The first was prepared, by high temperature calcination of a 3× selectivated catalyst at 1700° F., while the second (Comparative) was prepared by steaming a 4× selectivated catalyst for 3 hours at 990° F. These catalysts were then used to convert ethylbenzene in a xylene isomerization reactor. The feed is a xylene-containing feed, with 10% ethylbenzene, 1% para-xylene, 64% meta-xylene, and 25% ortho-xylene. The catalysts were first reduced in hydrogen, then lined out for 24 hours using this feed. The catalysts were then evaluated at temperatures of 820°–760° F. in 20° F. increments, at 20 WHSV, 10 WHSV and 5 WHSV using a 1/1 hydrogen/hydrocarbon ratio at 200 psig. The results are shown in Table 3 below.

TABLE 3

| Catalyst | High Temperature Calcined Catalyst | Steamed Catalyst |
|---|---|---|
| Yields (wt. %) | | |
| $C_5^-$ | 1.9 | 2.0 |
| Benzene | 5.4 | 5.6 |
| Toluene | 0.5 | 1.1 |
| Ethylbenzene | 1.2 | 1.1 |
| Para Xylene | 1.8 | 2.6 |
| Meta Xylene | 63.2 | 62.7 |
| Ortho Xylene | 26.0 | 25.1 |

TABLE 3-continued

| Catalyst | High Temperature Calcined Catalyst | Steamed Catalyst |
|---|---|---|
| Heavies ($C_{9+}$) | 0.0 | 0.0 |
| Ethylbenzene Conversion | 87.6 | 88.9 |
| Xylene Loss | 0.2 | 0.8 |
| Para Approach (PATE) | 3.0 | 7.6 |

These data show that the high temperature calcined catalyst effectively converts ethylbenzene. They also show that the xylene loss afforded over the high temperature calcined catalyst is lower than that afforded over the steamed catalyst.

The invention claimed is:

1. A method for modifying a catalytic molecular sieve which comprises:
   a) selectivating said catalytic molecular sieve by contacting with a silicon containing selectivating agent; and
   b) calcining the selectivated catalytic molecular sieve at high temperature calcination conditions comprising temperatures greater than 700° C., which conditions are sufficient to reduce acid activity as measured by alpha value and increase diffusion barrier of said catalytic molecular sieve as measured by the rate of 2,3-dimethylbutane uptake, as compared to the selectivated catalytic molecular sieve.

2. A method for modifying a catalytic molecular sieve for shape-selective hydrocarbon conversions which comprises:
   a) selectivating said catalytic molecular sieve by contacting with a silicon containing selectivating agent; and
   b) calcining the selectivated catalytic molecular sieve at high temperature calcination conditions comprising temperatures greater than 700° C., which conditions are sufficient to reduce acid activity as measured by alpha value and increase diffusion barrier of said catalytic molecular sieve as measured by the rate of 2,3-dimethylbutane uptake by at least 25%, as compared to the selectivated catalyst.

3. The method of claim 2 wherein said catalytic molecular sieve is selected from the group consisting of ZSM-5, ZSM-11, ZSM-12, ZSM-22, ZSM-23, ZSM-35, ZSM-48, ZSM-50, ZSM-57, ZSM-58, zeolite beta, MGM-22, MCM-36, MCM-49, MCM-56, mordenite, MCM-58, synthetic faujasite, natural faujasite, MCM-41, ALPO5, VPI-5, SAPO-5, SAPO-11, SAPO-30, SAPO-31, SAPO-34, ITQ-2, ITQ-3, ITQ-12, and ITQ-13.

4. The method of claim 3 wherein said catalytic molecular sieve is a silica-bound ZSM-5.

5. The method of claim 2 wherein said catalytic molecular sieve comprises a metal of a group selected from Group VIIIA, Group VIIA, Group VIA, Group VB, Group IVB, Group IIB, Group IIA, and Group IB of the Periodic Table.

6. The method of claim 2 wherein said catalytic molecular sieve comprises a hydrogenation metal selected from the group consisting of platinum, palladium, iron, nickel, gallium, zinc, molybdenum, and rhenium.

7. The method of claim 2 wherein said selectivating agent is selected from the group consisting of polysiloxanes, siloxanes, silanes, disilanes and alkoxysilanes.

8. The method of claim 2 wherein said selectivating is carried out by two to six treatments with a selectivating agent.

9. The method of claim 2 wherein said calcining is carried out under conditions sufficient to provide a catalytic molecular sieve having an alpha value of less than 700 and a diffusion barrier as measured by the rate of 2,3-dimethylbutane uptake of less than 270 ($D/r^2 \times 10^6$ sec$^{-1}$).

10. The method of claim 2 wherein said calcining is carried out under conditions sufficient to provide a catalytic molecular sieve having an alpha value ranging from 25 to 200 and a diffusion barrier as measured by the rate of 2,3-dimetylbutane uptake of less than 150 ($D/r^2 \times 10^6$ sec$^{-1}$).

11. The method of claim 2 wherein said calcining is carried out under conditions sufficient to provide a catalytic molecular sieve having an alpha value ranging from 5 to 25.

12. The method of claim 2 wherein said calcining is carried out at temperatures ranging from greater than 700° to 1200° C. for 0.1 to 12 hours.

13. The method of claim 12 wherein said catalytic molecular sieve is a silica-bound ZSM-5 and further comprising a hydrogenation metal selected from the group consisting of platinum, palladium, iron, molybdenum, and rhenium.

14. The method of claim 1 wherein said diffusion barrier is increased by at least 25%.

15. The method of claim 2 wherein said diffusion barrier is increased by at least 35%.

16. The method of claim 2 wherein said diffusion barrier is increased by at least 50%.

* * * * *